United States Patent [19]

Kreuzer et al.

[11] Patent Number: 4,937,449
[45] Date of Patent: Jun. 26, 1990

[54] DEVICE FOR THE INSPECTION OF COATED AND UNCOATED FILMS

[75] Inventors: Erwin Kreuzer, Grafing; Harald Pontow, Munich; Richard Zierl, Eichenau; Alfred Zuckermayr, Munich, all of Fed. Rep. of Germany

[73] Assignee: Agfa-Gevaert Aktiengessellschaft, Leverkusen, Fed. Rep. of Germany

[21] Appl. No.: 231,966

[22] Filed: Aug. 15, 1988

[30] Foreign Application Priority Data

Aug. 28, 1987 [DE] Fed. Rep. of Germany ....... 3728705

[51] Int. Cl.$^5$ .................. G01J 1/00; G01F 23/00; G01B 11/06
[52] U.S. Cl. .................. 250/351; 250/341; 250/339; 250/359.1; 356/382
[58] Field of Search .............. 250/341, 339, 358.1, 250/359.1, 351; 356/381, 382

[56] References Cited

U.S. PATENT DOCUMENTS

| | | | |
|---|---|---|---|
| 3,565,531 | 2/1971 | Kane et al. | 356/381 |
| 3,597,616 | 8/1971 | Brunton et al. | 250/341 |
| 4,274,091 | 6/1981 | Decker | 250/341 |
| 4,320,967 | 3/1982 | Edgar | 356/382 |
| 4,491,731 | 1/1985 | Funyu et al. | 250/358.1 |
| 4,542,297 | 9/1985 | Hold | 250/359.1 |
| 4,713,140 | 12/1987 | Tien | 356/381 |
| 4,733,078 | 3/1988 | Strum | 250/359.1 |

FOREIGN PATENT DOCUMENTS 0017905 1/1986 Japan .................. 356/381

Primary Examiner—Constantine Hannaher
Assistant Examiner—J. Eisenberg
Attorney, Agent, or Firm—Connolly & Hutz

[57] ABSTRACT

In a coated or uncoated film, variations in thickness as well as all possible casting errors may be dependably determined and evaluated, in that two light sources transmit modulated IR light wherein the modulation frequencies are different, wherein one light source transilluminates the film, while the other light source is arranged on the other side of the coating carrier, illuminates the latter obliquely and both the transilluminating and the reflected light bundles are conducted to a photo-receiver. The current signal arising in the photo-receiver is transformed into a current signal, amplified and feeds two electronic filters circuited in parallel, which free the signals from their modulation frequency, after which both signals are separately rectified. Subsequently the signal originating from the transmitted light portion is delogarithmized and forms a statement concerning the thickness of coating, while the light originating from the reflected portion evaluates surface errors. In this manner a separate evaluation of both kinds of error is possible.

9 Claims, 3 Drawing Sheets

DEVICE FOR THE INSPECTION OF COATED AND UNCOATED FILMS

The invention relates to a device for the inspection of preferably sheet-shaped coated and uncoated films by optoelectronic means in respect of surface condition, thickness, variations in thickness, coating condition or gaps in the coating.

In the manufacture of photographic material or magnetic recording materials, preferably flexible films, consisting for example of cellulose triacetate or of polyethyletherephthalate, are used as coating carriers. It is required therein that the film sheets both before and after coating be checked in respect of evenness and surface condition, as variations in the thickness of coating or surface errors are known to influence both the recording and the reproduction quality of the recording material considerably. Such controls are customarily carried out by spot checks. for example measurements of coating thickness by mechanical methods or surface investigations by optical interference methods.

In DE-OS 27 24 919, 29 09 400, 29 35 716, 31 49 709 and 32 48 157 infra-red light is used for coating thickness measurement, either by transmission or reflection or interference measurement. DE 16 23 196 suggests polarised infra-red light. DE 31 36 887 uses an interferometer arrangement as measuring method. In DE 29 07 620 it is recommended that a fluorescing material be mixed into the coating be measured and the fluorescing light measured as a measure of the coating thickness. In DE 23 33 326 the measuring light is split into a number of light bundles which irradiate a film and thus enable a measurement of coating thickness at several points. In DE 23 55 185 and EP 0 211 654 laser light is suggested for the measurement of coating thickness. In the first-named text, the laser ray is directed in sequence vertically onto a reference plane and on to the object of measurement, and the differential measurement is evaluated as a measure of the coating thickness. In the last-named text the coating thickness is determined by guiding the film to be measured over a roller which is arranged opposite an edge, so that the gap thus arising is a measure of the coating thickness. In DE 22 54 910 it is explained that a long term drift in the measuring arrangement may be avoided in that the measuring light is separated and a portion of the light used as comparison ray path eliminates light variations. The use of modulated light for coating thickness measurement is known from DE 29 28 997.

U.S. Pat. No. 3 956 630 describes a process for measuring the coating application on paper sheets, in which a fluorescent substance is added to the coating mass, the sheet is illuminated with UV light and the diffusely reflected fluorescent light is measured. A similar arrangement, however without fluorescing substance, is described in DE-GM 82 02 548.

The measuring arrangements described are, however, not suitable for on-line measurements of film sheets, which are unrolled and rolled up at high speed in a casting device, or they are too complicated, or they do not give sufficient accuracy. The object was therefore to find a measuring device for the checking of coated or uncoated flexible films, which measures the thickness as well as thickness variations of a film on-line simultaneously tests the surface condition and registers casting failures delivers measurement results across the total sheet width of the film simultaneously possesses sufficiently small measuring regions to confirm errors even of small dimensions as well registers the results of measurement simultaneously (on-line), so that an error may be localized gives constant results even in long-term measurement.

The object was solved according to the invention with a device for the inspection of the quality of preferably sheet-shaped uncoated or coated films by optoelectric means, consisting of an infrared light source, which is charged with modulated light, a photoreceiver and evaluating electronics. Further details of the invention emerge from the sub-claims, the description and the drawings.

The invention will now be more closely explained with reference to drawings; in which.

The inventive idea consisted substantially in measuring, with a single photo receiver (3), an IR light bundle reflected at the coated or coated sample and an IR light bundle transilluminating the sample of the same point and, in order to be able to evaluate both signals separately in an appropriate evaluating electronics, modulating both light bundles, which originate from the two IR light sources, with different frequencies. In this manner, thickness of coating, variations in thickness of coating, as well as casting errors and surface errors may be determined. Thus, among other things, failures of casting may also be simply distinguished from surface errors such as abrasion, deformations, creases and so forth.

1. Optical Arrangement

As light sources:

Lasers, which yeild radiation in the IR region directly or by frequency multiplication, or Incandescent lamps with shares of radiation in the IR region, preferably from 1 to 3 um. With these light sources shorter-waved portions of radiation are to be filtered out by filters.

LED light sources may be used.

Figure 1:
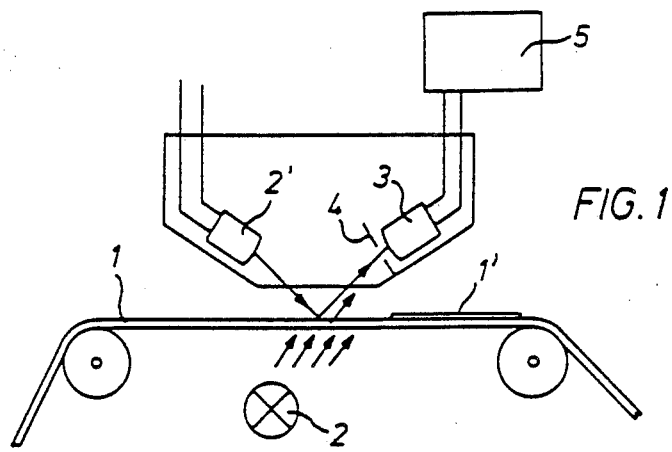
FIG. 1 shows a schematic side view of the device according to the invention

As may be seen from FIG. 1, the light coming from the light source (2) irradiates the uncoated or coated film (1), wherein the light passing through is picked up by a photo-receiver (3). Simultaneously, a second light source (2') illuminates the surface of the film (1) or of the coating (1') obliquely at an angle of incidence of 10° to 80 ° and the reflected light, equally, strikes the photo-receiver (3). In front of the latter a pin diaphragm (4) is arranged, which brings it about that, independently of small changes inseparation of the film (1) from the photo-receiver (3), the former sees only one part of the homogeneously illuminated and diffusely radiating surface of the proportion of transmitted light. Small variations in separation due to uneven running of the coating carrier thus do not enter into the result of measurement.

Something similar is true for the reflected light portion. The focussing of the receiver by a lens or a pin aperture is smaller than the homogeneously illuminated surface, so that here too small variations of separation are not or only insubstantially observable.

Figure 2:
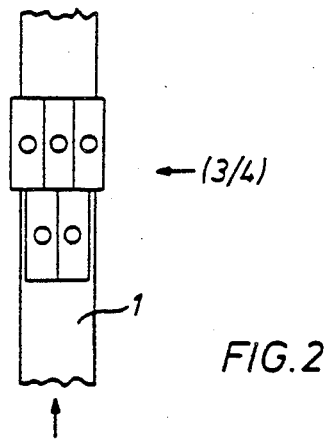
FIG. 2 shows a top view of the device according to the invention

As the preferred object now consists in measuring the characteistics of a film track running in the casting device on-line over its whole width, either individual arrangements of point-like light sources (2,2') and receivers, or preferably a tubular incandescent lamp, for example of the Linestra type, which is arranged across the motion of the track, may be used as light source (2), so that the whole track width is irradiated by this lamp from above or from below. The light may be directed parallel or converging onto the film track by reflectors or centering lenses, so that in this manner the film is illuminated over its complete track width. In this case, the light current passing through is picked up by a number of photo-receivers, which are arranged on the opposite of the film. The number of the photo-receivers determines the scanning density that can be stretched right up to the gap-free determination of the total track width of the film. The light reflected on the upper surface of the coating originates preferably from LED cells (2'). FIG. 2 shows a useful arrangement of the light sources or possible pin diaphragms and phot receivers, wherein two coatings of photo receivers are arranged one behind the other in the direction of movement of the film, each displaced in relation to the other. Light source (2') (LED) and photo-receiver are obtainable on the market as finished construction elements.

Both light sources are frequency modulated; this measure is necessary in order to obtain no interfering portions due to the existing light and so forth, by means of filtering out the modulated wave length in the electronic section. The modulation may be achieved mechanically, optically or electronically by means which are known from the prior art. The modulation frequency is given by the frequency response of the photo-receiver, wherein 100 Khz may be achieved without difficulty in order to be able to evaluate the signals given via the reflected or possibly transmitted light separately, both light sources (2,2') are modulated at different frequencies and evaluated separately in an evaluating electronics yet to be explained later. The resolution of rotation in the direction of movement depends on the magnitude of the frequency of modulation and the running speed of the film (modern casting processes are driven at speeds greater than 1.5 m/sec). Thus the resulution at a casting speed of 5 m/sec and a modulation frequency of 100 Khz is 25 um.

The distribution of wavelength of the IR light is to be chosen so that depending on the height of absorption of the coating carrier and of the coating poured thereon, clear changes in measurement values result from variations in thickness. This is provided for example with a polyethylene terephthalate film and magnetic coating casted thereon depending on magnetic pigment (metal powder, chromium dioxide, magnetite or $\gamma$-$FE_2O_3$) at a wave length of 1 to 3 um.

In the process, on the other hand, no excessively strong heating of the film by means of the irradiating light source (2) need be feared, as the proportion of constant light of the light source (2') determines the operating point of the photo-receiver (3). This porportion, which would substantially add to the heating of the film, may drop out for the signal from the light source (2). Light source (2) may possess the minimal possible proportion of constant light. The modulated transmitted light signal arriving at the secondary side is added to the reflection signal determined by the operating point.

2. Signal Evaluation

Figure 3:
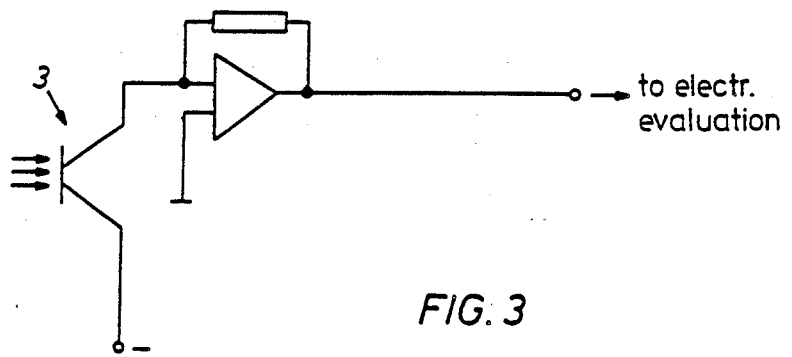
FIG. 3 shows a basic circuit diagram for converting the current signal in to a voltage signal.
Figure 4:
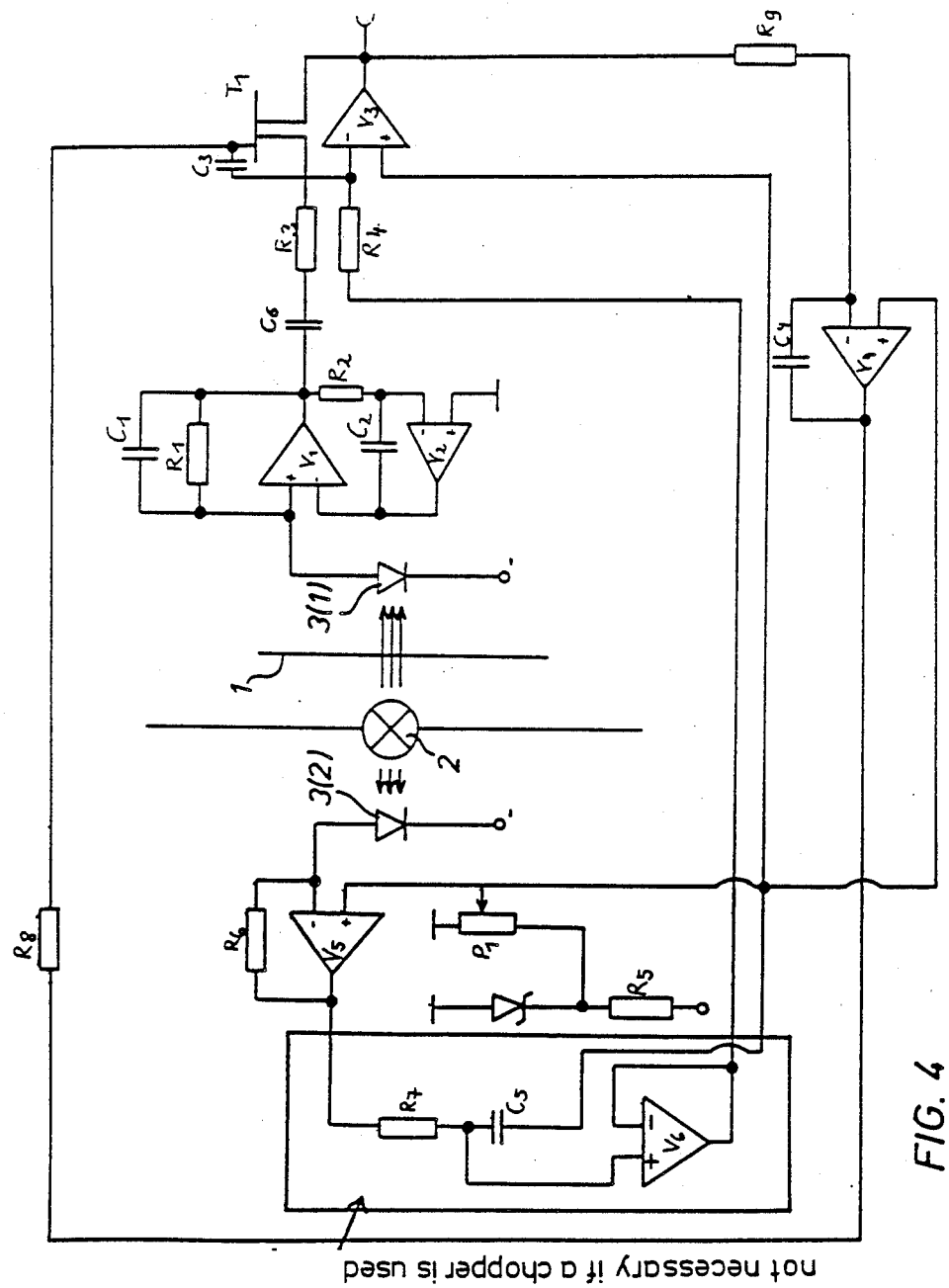
FIG. 4 shows a basic circuit diagram of the evaluation electronics according to the invention, in respect of zero-point, and amplification control.
Figure 5:
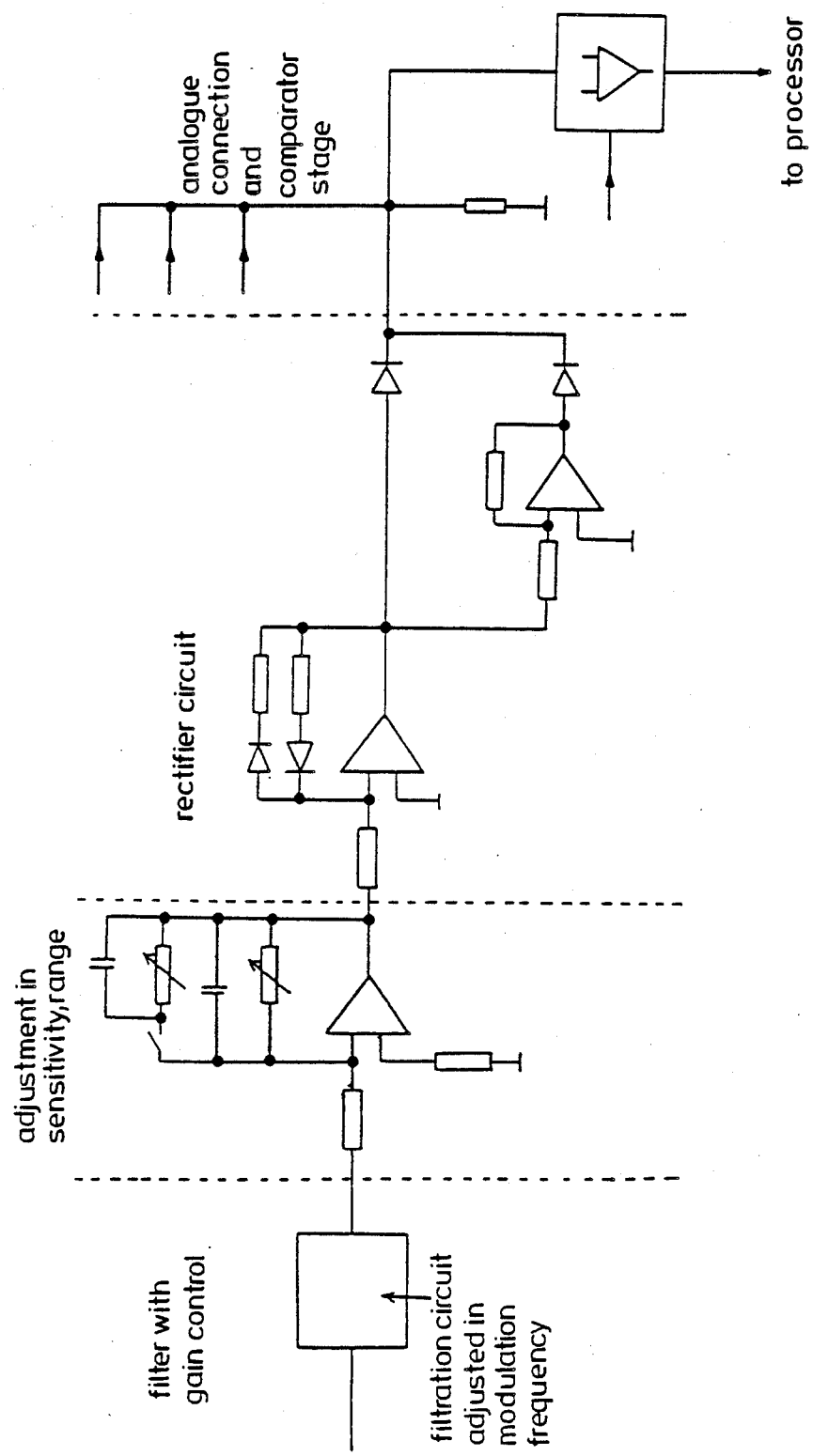
FIG. 5 shows a basic circuit diagram of the signal processing steps for the reflected light signals.

As already explained, the transmitted light and the reflected light proportions are evaluated separately. The electronic evaluation of the signal received by receiver (3) is essentially represented in FIGS. 3 to 5, and also runs substantially analogously to the evaluation according to the corresponding German application of the applicant, ref. P 37 28 704. First (FIG. 3) the current signal produced in receiver (3) is transformed into a voltage signal, which is subsequently amplified in a voltage amplifier. In the process, long-term light variations of the light source, as represented in FIG. 4, may be compensated by an appropriate circuit. More precise details may also be gathered from the corresponding German application, ref. No. P 37 28 704. The output signal is now conducted to two parallel electronic filters, of which one filter is represented in FIG. 5. These filters are tuned to the prevailing modulation frequency of the transmitting or possibly reflecting light, so that in this manner a separate evaluation is possible. The further signal processing is only represented in FIG. 4 for the case of the transmitting light, wherein after the filter an adjustment of the region of sensitivity is provided, subsequently a rectifier stage, an impedance stage and a delograithmization stage. The delogarithmized signal is, as explained in the corresponding application, P37 28 704, already referred to, in inverse proportion to the coating thickness of the coated or possibly coated film. The proportion of the reflected light is similarly evaluated, however, the delogarithmization stage may be dispensed with.

The measurement values obtained are simultaneously present for all measurement traces. Depending on width resolution desired, they may be grouped in more or less small groups. The grouping into groups may take place as may be seen from FIG. 4 (rectifier circuit, impedance stage and analogue connection). The connected signals are evaluated in a comparator stage. Subsequently, a processor undertakes the evaluation. Evaluation may occur either as a formatted expression of error, or in the form of regulating signals conveyed to a regulating process or given to other computers for static further processing. The process as represented above is to be seen as the principal solution. It is to be specified depending on the desired use. The specification takes place through varying choice of the light wave lengths (may vary between transmitted and reflection light), or by variable specification of the coating thickness or of the film thickness as constant and through type-specific calibration magnitudes. If, for example, the transmitted light portion changes for a determined material, while the reflected light portion remains completely or nearly unchanged, then this shows a variation in thickness of the film or of the coating cast thereon. In order now to differentiate between whether a variation of the thickness of the film or of the coating cast thereon is present, for example the measured value of the transmitted light may be placed in relation to the value obtained according to the corresponding application P 37 28 704 which is directly proportional to the coating thickness of the uncast film. By forming the difference of both value after prior calibration of the device and assignment of the measurement locations it can be thus clarified whether an error of coating is present or whether only the thickness of the film has changed. Casting errors are distinguished by their signal height by virtue of the total transparency. They are easily separated by the use of further comparator.

If, conversely, the proportion of transmitted light does not change, or change little, while the proportion of reflected light wavers considerably, this shows surface errors such as scratches or abrasive particles. It is clear that a gap-free recognition and assignment of all occurring coating errors is made possible.

The invention may be used for checking all possible coating carriers in question, such as paper or transparent films, upon which photographic or magnetic or other coating compositions may be cast.

We claim:

1. Device for the inspection of the quality of preferably sheet-shaped uncoated or coated films by optoelectronic means, consisting of an infra-red light source which is charged with modulated light, a photoreceiver and evaluating electronics, characterized in that
   a light source (2) transilluminates a film from a first reverse side (1) and a photo-receiver (3) measures that light transmitted
   simultaneously a light source (2') obliquely illuminates the film from a second obverse side, wherein its light strikes the same position of the film as that at which the light transmitted by the light source (2) leaves the upper surface of the coating and wherein the light reflected from the light source (2') at the upper surface of the coating also reaches the photo-receiver (3)
   a pin diaphragm (4) is arranged betwen film and photo-receiver
   light sources (2,2') are modulated at different frequencies
   in an evaluation electronics (5) the current signal produced in the receiver (3) is transformed into a voltage signal, which is amplified in a voltage amplifier and subsequently fed into two electronic filters switched in parallel to each other in order to separate the signal paths, wherein the signals are subsequently separately rectified.

2. Device according to claim 1, characterized in that the film consists of polyethelene terephthalate, which may be coated with a magnetic coating, and that the infra-red light lies in the wavelenght region of 1 to 3 um.

3. Device according to claim 1, characterized in that the light source (2) is a tubular incandescent lamp, which is arranged perpendicular to the direction of movement of the film and parallel to the plane of the film and photoreceivers on the obverse side of the film, parallel to the tubular incandescent lamp.

4. Device according to claims 1, 2 or 3, characterized in that the light source (2') is at least one LED cell.

5. Device according to claims 1, 2 or 3, characterized in that the light emerging from the light sources (2,2') is modulated by means for modulating with a frequency of 0.05 to 100 Khz.

6. Device according to claims 2 or 3, characterized in that the current signal arising in the receiver (3) is fed into means regulating a zero-point comprised of an input amplifier and an integration amplifier.

7. Device according to claims 1, 2 or 3 characterized in that a part of the light going out from the light sources is conducted to receivers, which feed the current signal into an amplifier, the outgoing signals are freed in an RC element from the modulation-alternating current voltage and the resulting signals effect a change in amplification at the amplifier via transistors utilizable as feedback resistors.

8. Device according to claims 1, 2 ro 3, characterized in that the individual measurement signals, after rectification, are gathered together via analogue "or" —connecting circuits into any group and evaluated group wise.

9. A device as claimed in claim 1 wherein the signal originating from the light source is delogarithized.

* * * * *